(12) United States Patent
Nguyen (10) Patent No.: US 8,550,664 B1
(45) Date of Patent: Oct. 8, 2013

(54) HANDS-FREE FILTER ASSEMBLY

(76) Inventor: Ronald C. Nguyen, Fountain Valley, CA (US)

( * ) Notice: Subject to any disclaimer, the term of this patent is extended or adjusted under 35 U.S.C. 154(b) by 259 days.

(21) Appl. No.: 12/696,059

(22) Filed: Jan. 29, 2010

Related U.S. Application Data (63) Continuation-in-part of application No. 12/229,365, filed on Aug. 22, 2008.

(51) Int. Cl.
*F21V 17/02* (2006.01)
*F21V 9/00* (2006.01)

(52) U.S. Cl.
USPC .................. 362/282; 362/293; 362/323

(58) Field of Classification Search
USPC ........... 362/105, 106, 253, 449, 451, 277, 362/282–284, 293, 319, 321–324; 359/892, 359/813; 351/213, 215, 221
See application file for complete search history.

(56) References Cited

U.S. PATENT DOCUMENTS

| | | | | |
|---|---|---|---|---|
| 1,688,113 A | * | 10/1928 | Bornkessel | 362/105 |
| 1,980,101 A | * | 11/1934 | Schneider | 2/10 |
| 2,333,541 A | * | 11/1943 | Madan | 362/208 |
| 2,414,338 A | * | 1/1947 | Simmon et al. | 362/293 |
| 2,614,783 A | * | 10/1952 | Spear | 248/226.11 |
| 2,893,379 A | * | 7/1959 | Springer | 362/105 |
| 4,274,128 A | * | 6/1981 | Malis | 362/105 |
| 4,763,986 A | * | 8/1988 | Sego | 359/798 |
| 5,289,350 A | * | 2/1994 | Gehrt | 362/293 |
| 5,479,293 A | * | 12/1995 | Reed | 359/432 |
| 6,116,729 A | * | 9/2000 | Huang | 351/41 |
| 6,761,467 B2 | * | 7/2004 | Matthews et al. | 362/282 |
| 7,128,436 B2 | * | 10/2006 | Bensinger et al. | 362/449 |
| 7,172,312 B2 | * | 2/2007 | Chen | 362/202 |
| D589,545 S | * | 3/2009 | Murphy et al. | D16/135 |
| D600,728 S | * | 9/2009 | Braganca et al. | D16/135 |
| 7,677,751 B2 | * | 3/2010 | Kinsman et al. | 362/105 |
| 7,710,569 B2 | * | 5/2010 | Zuluaga | 356/445 |
| 2008/0106906 A1 | * | 5/2008 | Lewsadder et al. | 362/322 |

* cited by examiner

*Primary Examiner* — Alan Cariaso (57) ABSTRACT

A hands-free filter assembly suitable for use with a loupe light is described. The hands-free filter assembly includes a filter that moves between an in-use position, where it is filtering light from the loupe light, and a non-use position, where it is not filtering light from the loupe light. The filter can be moved between the in-use position and the non-position without manual manipulation.

17 Claims, 12 Drawing Sheets

HANDS-FREE FILTER ASSEMBLY

CROSS-REFERENCE TO RELATED APPLICATIONS

This application is a continuation-in-part of pending patent application Ser. No. 12/229,365, entitled "COMPACT LOUPE LIGHT," filed Aug. 22, 2008.

BACKGROUND

Loupe lights are lights attached to dental loupes or other eyewear to illuminate an area of interest. Some loupe lights may use a fiber optic cable that transmits light from a light source.

Loupe lights are often bulky and heavy and uncomfortable to wear for prolonged periods of time. Loupe lights may restrict movement, or cause the loupe to move or become dislodged when the user turns or moves. Loupe lights may generate large amounts of heat and become very warm with prolonged use.

Other loupe lights use a self-contained light source and draw power from a remote power supply. These loupe lights are powered by a wire. Wire protection is designed to prevent the wire from being detached from the loupe light when the wire is pulled on, either through use or by accident. Wire protection may be afforded by a knot in the wire, or a crimp or screw securing the wire.

Filters are used with loupe lights for a variety of purposes, such as preventing the curing of light-cured materials. Filters may be attached and detached as necessary. Alternatively, filters may have an attachment that allow a user to manually move the filter between an in-use position and a non-use position. However, the user may not have a free hand, or the user may have soiled hands, making it difficult to move the filter or move the filter without soiling the filter.

What is needed is a filter that can be moved between an in-use position and non-use position without requiring the user to touch it.

SUMMARY

A hands-free filter assembly is described. The hands-free filter assembly includes a filter, a filter attachment capable of being coupled to a loupe light, a filter swivel coupling the filter to the filter attachment, wherein the filter may be moved between an in-use position and a non-use position without manual manipulation, and a filter stop coupled to the filter attachment, the filter stop capable of maintaining the filter in the non-use position.

DETAILED DESCRIPTION OF PREFERRED EMBODIMENTS

Figure 1A:
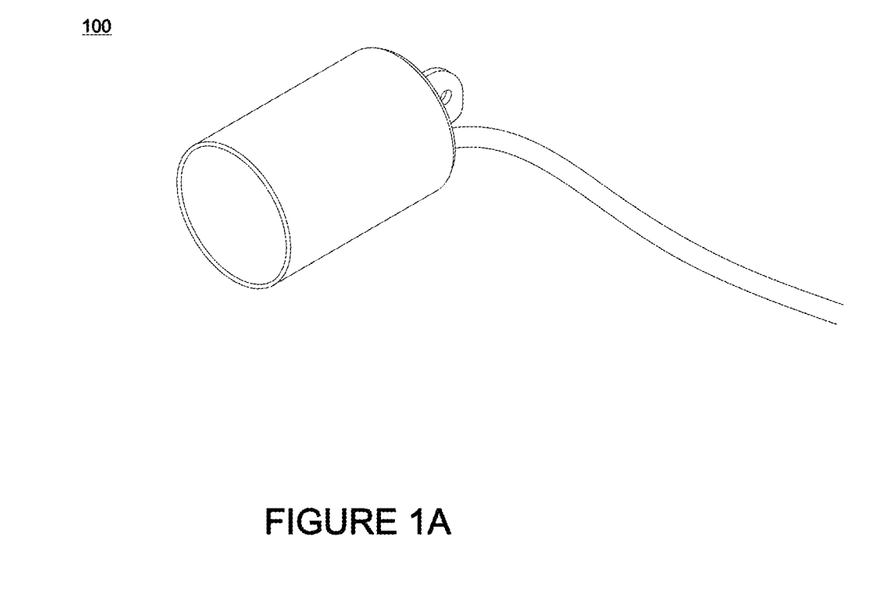
FIGS. 1A-1B show assembled and exploded views of one embodiment of a compact loupe light.
Figure 1B:
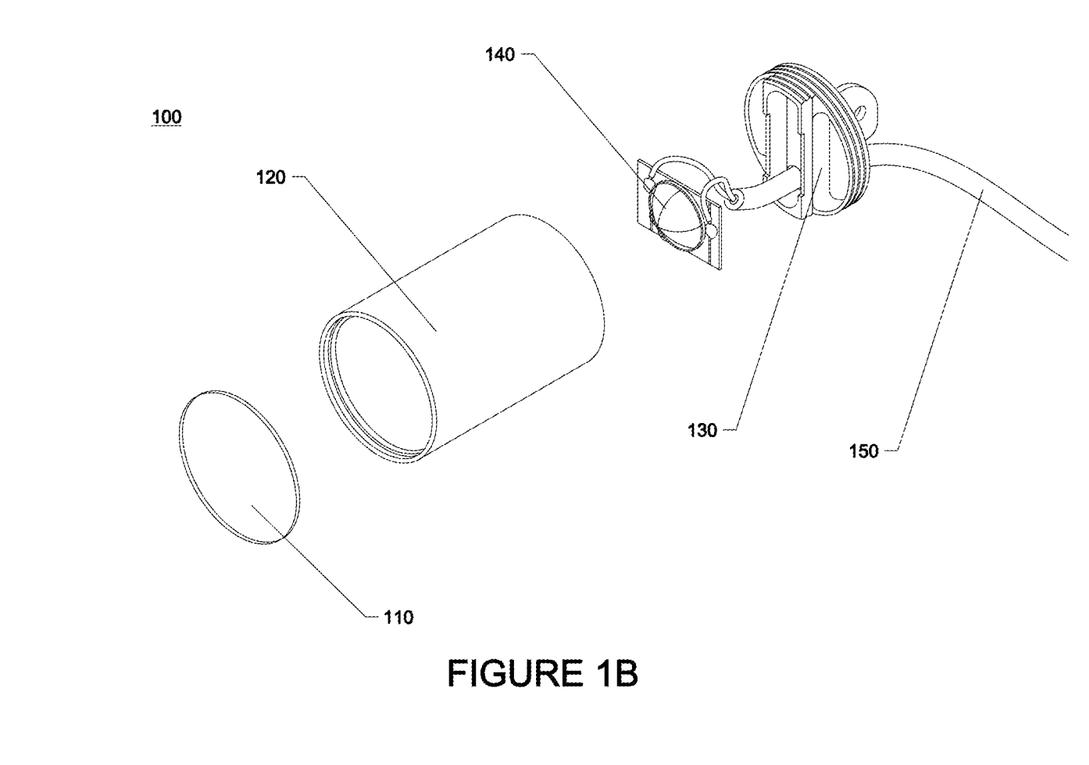

FIGS. 1A-1B show assembled and exploded views of one embodiment of a compact loupe light 100. Compact loupe light 100 includes a lens 110, a body 120, an end piece 130, a light source 140, a wire 150, and an adhesive 160.

Lens 110 may be any suitable shape or configuration, and may be manufactured out of glass, plastic, or any other suitable material. In the embodiment shown, lens 110 is a biconvex singlet lens. Lens 110 may be coupled to body 120 by a press fit, threading, adhesive, or any other suitable method of coupling. In the embodiment shown, lens 110 is press fit to a front end of body 120.

Figure 2:
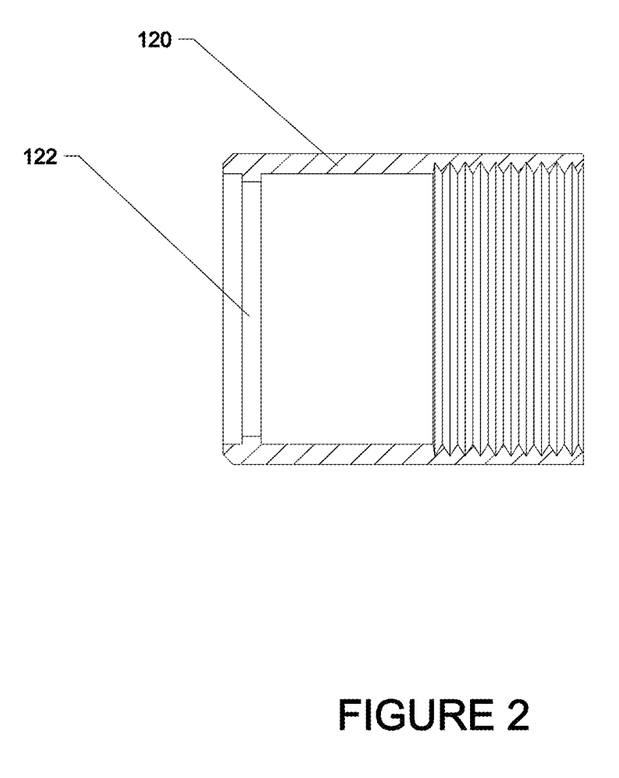
FIG. 2 shows a side cross-sectional view of one embodiment of a body of a compact loupe light.

FIG. 2 shows a side cross-sectional view of one embodiment of a body 120 of a compact loupe light 100. Body 120 may be cylindrical, conical, partially conical or any suitable shape or configuration. In the embodiment shown, body 120 is substantially cylindrical. Body 120 may be manufactured out of metal, plastic, or any other suitable material. In one embodiment, body 120 is manufactured out of 6061 aluminum alloy. Body 120 may be anodized or otherwise colored dark to reduce glare. In the embodiment shown, the front end of body 120 may include a lens stop 122 against which lens 110 is seated. Lens stop 122 may be one or more protrusions inside body 120, or lens stop 122 may be continuous. In the embodiment shown, a rear end of body 120 is threaded to receive end piece 130.

Figure 3:
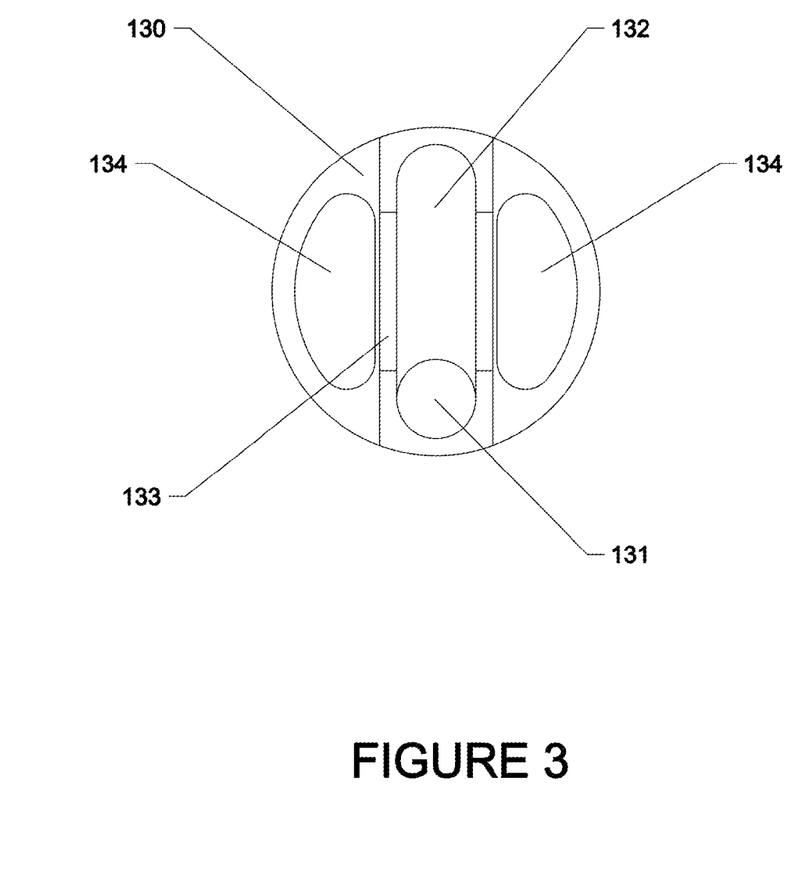
FIG. 3 shows a front view of one embodiment of an end piece of a compact loupe light.

FIG. 3 shows a front view of one embodiment of an end piece 130 of a compact loupe light 100.

End piece 130 may be any suitable shape or configuration, and may be manufactured out of metal, plastic, or any other suitable material. In the embodiment shown, end piece 130 is substantially cylindrical and is manufactured out of 6061 aluminum alloy. End piece 130 may be coupled to body 120 by press fit, threading, adhesive, or any other suitable method of coupling. In the embodiment shown, end piece 130 is threaded and configured to be coupled to the rear end of body 120, which is also threaded.

End piece 130 includes a hole 131 and an open channel 132 formed in end piece 130. Hole 131 is positioned within channel 132. In the embodiment shown, hole 131 is substantially circular and has a size substantially similar to that of wire 150. In the embodiment shown, channel 132 has a width substantially similar to that of wire 150. Channel 132 is also sufficiently deep to accommodate wire 150. Channel 132 is formed by channel walls 133. End piece 130 may have portions 134 removed to save weight.

Channel 132 may include other features which allow wire 150 to be held more securely in channel 132. For example, channel 132 may have ribs which extend partially into channel 132 and allows wire 150 to be held more securely in channel 132. As another example, channel 132 may have a surface treatment which allows wore 150 to be held more securely in channel 132.

Channel 132 may also have a cross-section which allows wire 150 to be held more securely in channel 132. Channel 132 may have cross-section that is wider at a top of channel 132 than at a bottom of channel 132. Channel 132 with this "wedge" cross-section allows wire 150 to be held more securely in channel 132 as wire 150 is pressed down into channel 132.

Figure 4A:
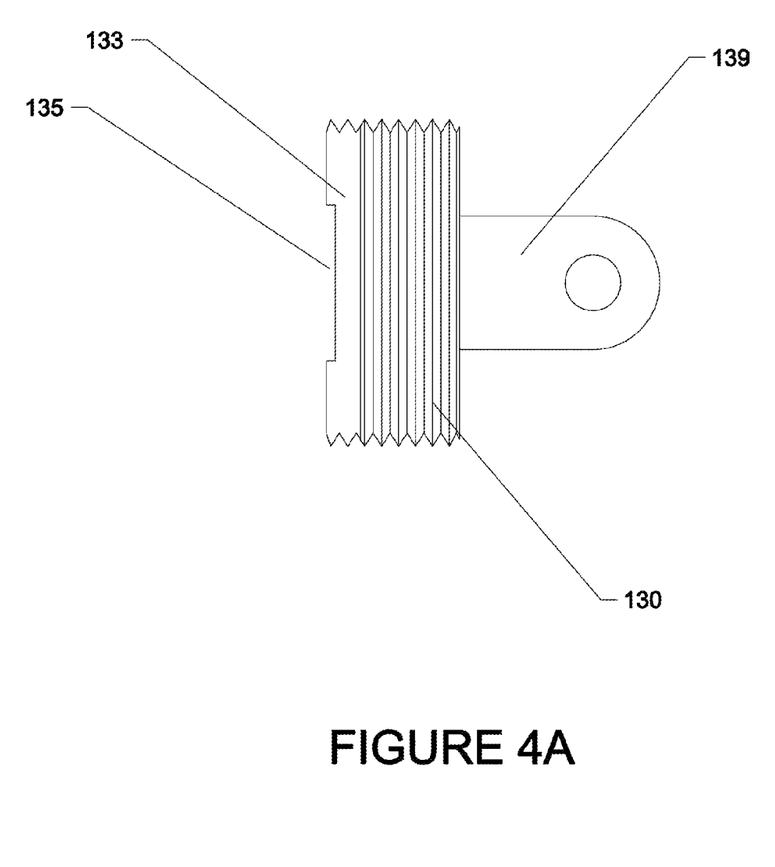
FIGS. 4A-4C show side and cross-sectional views of one embodiment of a compact loupe light.
Figure 4B:
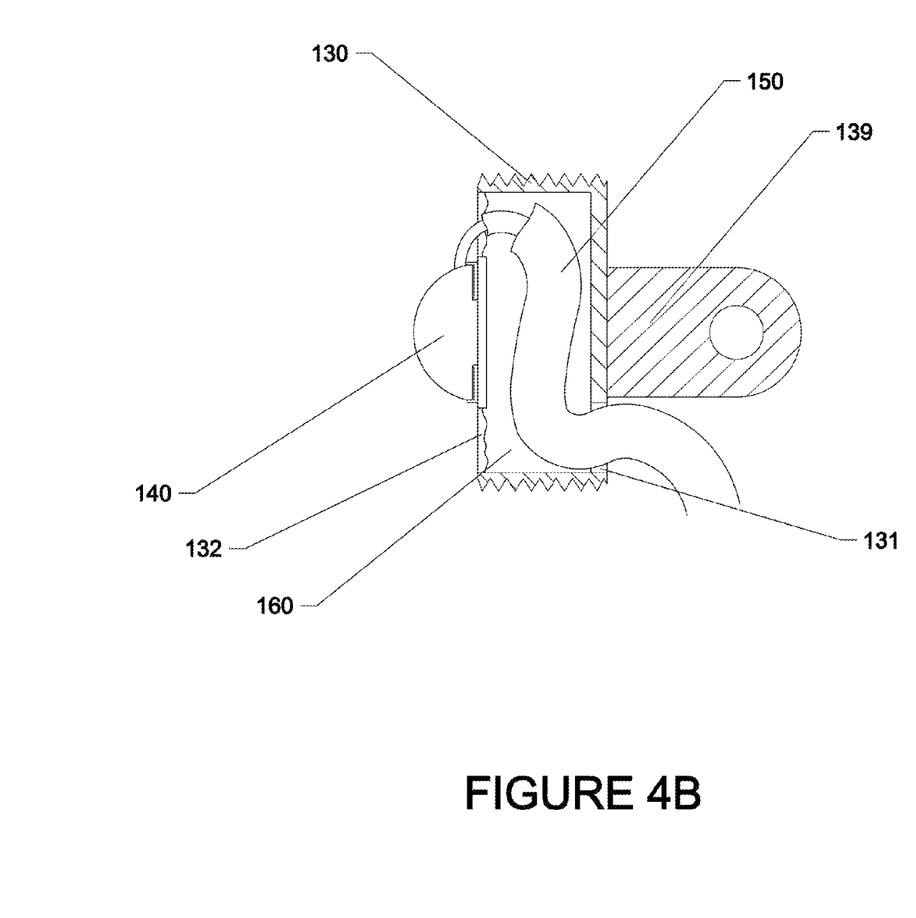
Figure 4C:
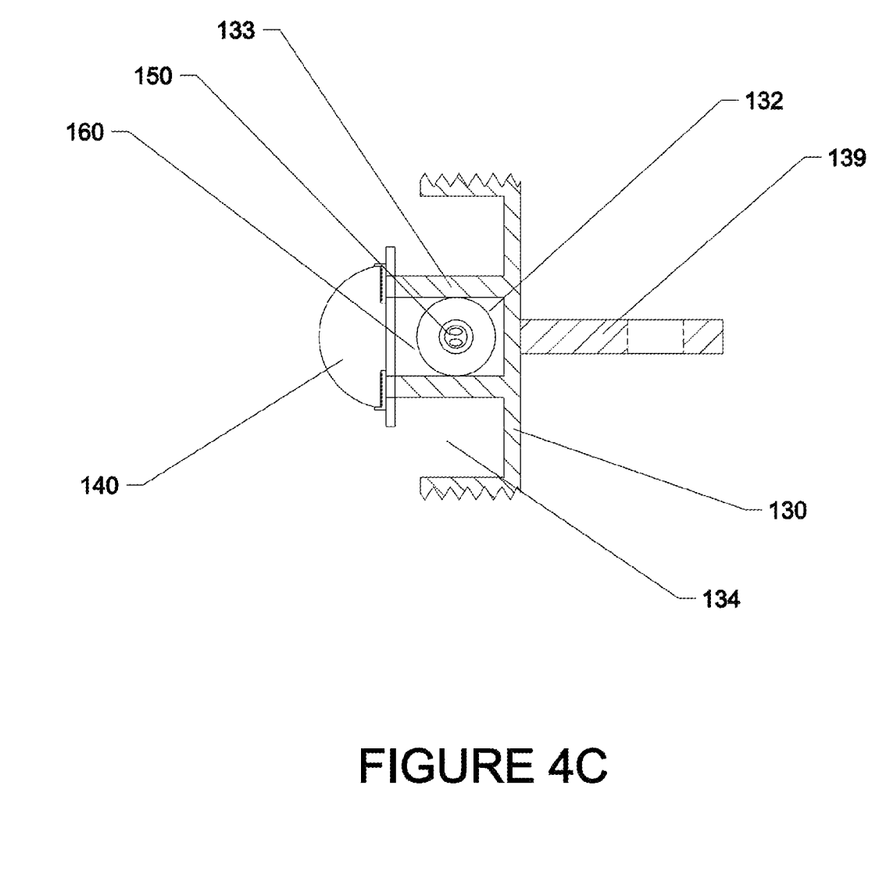

FIGS. 4A-4C show side and cross-sectional views of one embodiment of an end piece 130 of a compact loupe light 100.

Channel walls 133 may be configured to be coupled to light source 140. In the embodiment shown, channel walls 133 include indentations 135 configured to assist in properly positioning or securing light source 140.

End piece 130 may have a mounting tab 139 which facilitates the coupling of compact loupe light 100 to a loupe. Mounting tab 139 may be used with different adapters in order to adapt compact loupe light 100 for use with different types of loupes.

Light source 140 may be any suitable source of light. In the embodiment shown, light source is an LED light mounted on a circuit board. Light source 140 may be a Cree XLamp 7090 XREWHT-L1-0000-X0D01 or a Cree XLamp 7090 XRE-WHT-L1-WH-R2-0-01.

Wire 150 may be of any suitable shape or configuration. In the embodiment shown, wire 150 is substantially cylindrical and includes two conductors and an insulating cover. Wire 150 may be coupled to light source 140 by soldering or any other suitable method of coupling. Wire 150 may be configured for connection to a power source.

Wire 150 passes through hole 131 and makes a bend before passing through at least portion of channel 132. The bend may be at least 75 degrees, but is preferably 90 degrees or greater.

Adhesive 160 at least partially fills channel 132. Adhesive 160 allows wire 150 to be held more securely in channel 132. Adhesive 160 fills channel 132 sufficiently to contact light source 140. Adhesive 160 allows light source 140 to be coupled more securely to end piece 130. Adhesive 160 may be Arctic Silver Arctic Alumina.

Adhesive 160 is electrically insulating. Electrical current from wire 150 will not conducted by adhesive 160. Adhesive 160 is also thermally conducting. Thus, waste heat from light source 140 is carried away by adhesive 160 and into end piece 130 and body 120. Adhesive 160, end piece 130, and body 120 thus act as a heat sink for light source 140.

Wire 150 is thus held in place by a combination of hole 131, channel 132, the bend created as wire passes through hole 131 and into channel 132, adhesive 160, and light source 140. This provides wire protection to wire 150 and strain relief to light source 140 in an effective and compact manner.

Figure 4D:
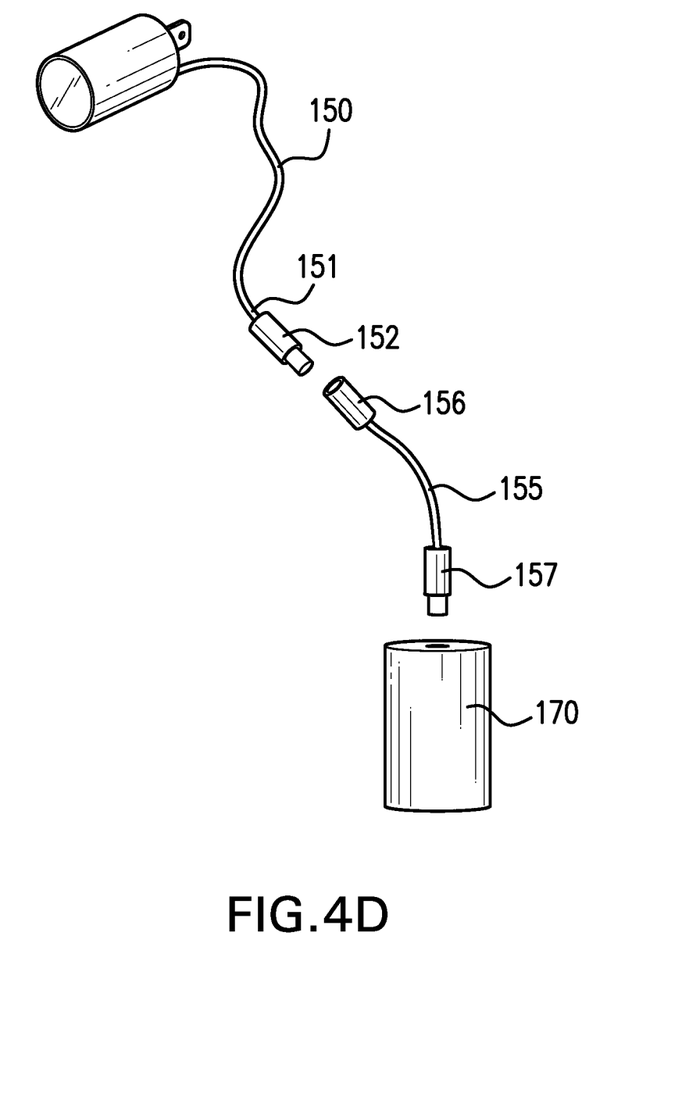
FIG. 4D shows one embodiment of a wire for a compact loupe light.

FIG. 4D shows one embodiment of wire 150. Wire 150 may include a plug 152 configured to be coupled to a power source 170. A portion 151 of wire 150 near plug 152 may fail from fatigue or extended use. In one embodiment of wire 150, a replaceable extension wire 155 may be provided. Extension wire 155 includes a light coupling 156 configured to be coupled to the end of wire 150 at plug 152. Extension wire 155 also includes a power source coupling 157 configured to be coupled to power source 170. Extension wire 155 is thus coupled between wire 150 and power source 170. Extension wire 155 may be of any suitable length. If extension wire 155 fails, then the cost of replacing extension wire 155 is less than that of replacing wire 150 of compact loupe light 100.

Figure 5:
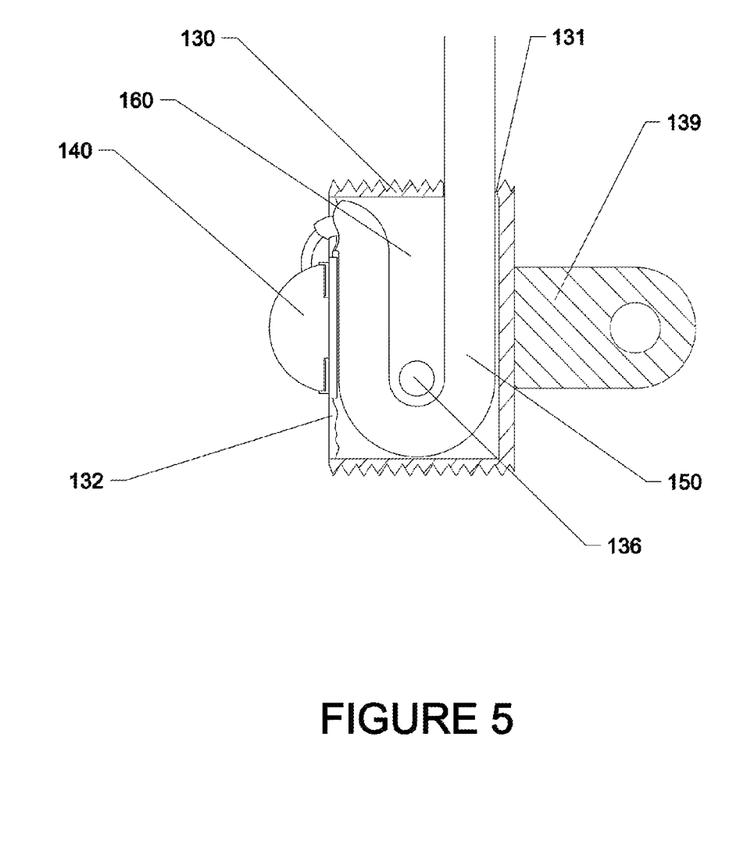
FIG. 5 shows a cross-sectional view of another embodiment of a compact loupe light.

FIG. 5 shows a cross-sectional view of another embodiment of an end piece 130 of a compact loupe light 100.

Hole 131 is positioned on a side of end piece 130. Wire 150 passes through hole 131 and at least a portion of channel 132, bends around a pin 136, and passes through another portion of channel 132.

Compact loupe light 100 can thus be made lightweight and compact. For example, compact loupe light 100 can be made to have a diameter of 0.65 inches or less, which is about the same as a dime, and a length of 0.76 inches or less. The compact loupe light 100 can be made to have a weight of 0.18 ounces or less, which is approximately the weight of a nickel.

Figure 6:
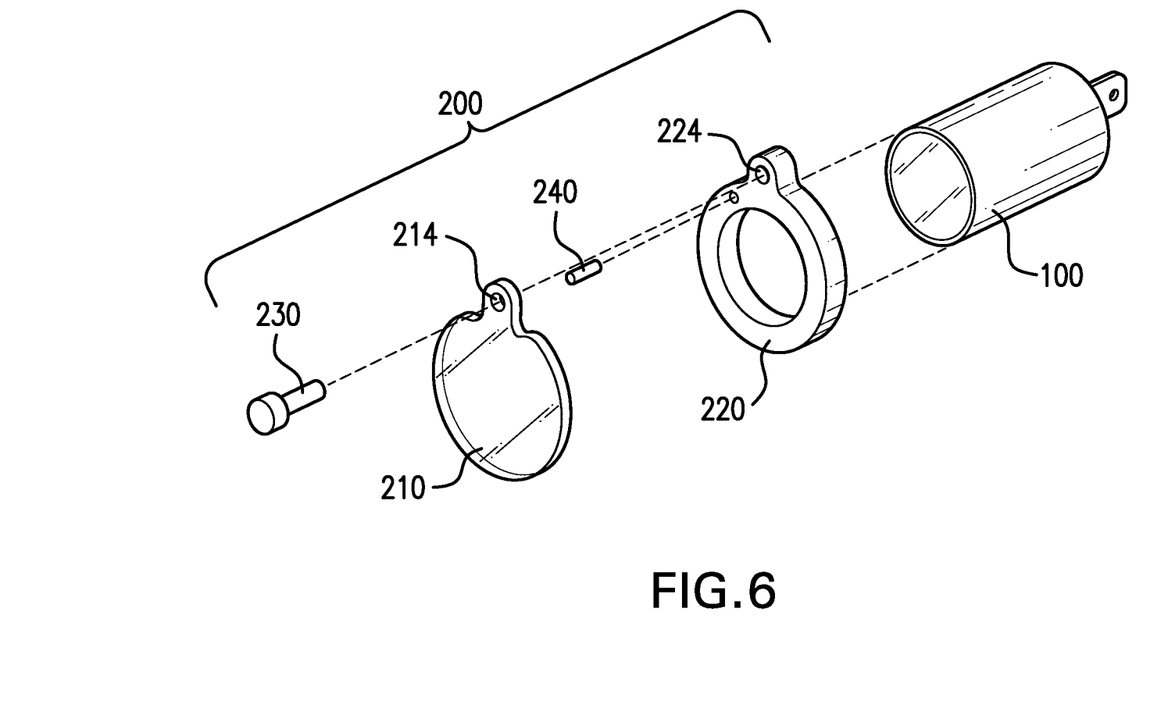
FIG. 6 shows an exploded view of one embodiment of a hands-free filter assembly.

FIG. 6 shows an exploded view of one embodiment of a hands-free filter assembly 200. Hands-free filter assembly 200 includes a filter 210, a filter attachment 220, a filter swivel 230, and a filter stop 240.

Figure 7:
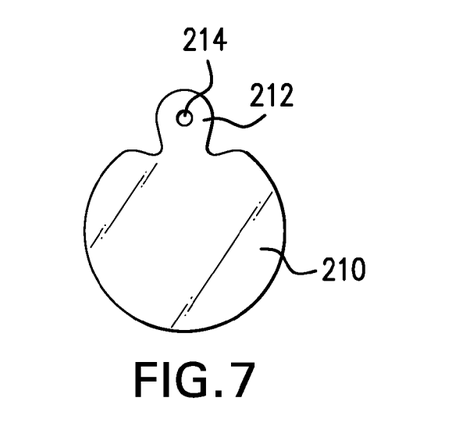
FIG. 7 shows one embodiment of a filter.

FIG. 7 shows one embodiment of filter 210. Filter 210 is made out of a suitable filtering material. Filter 210 is substantially circular with a tab 212 which defines a filter hole 214.

Figure 8A:
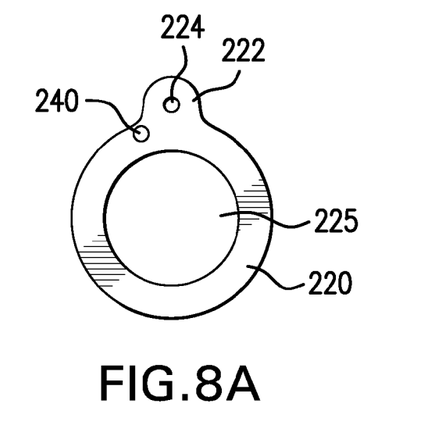
FIGS. 8A-8B show two embodiments of a filter attachment.
Figure 8B:
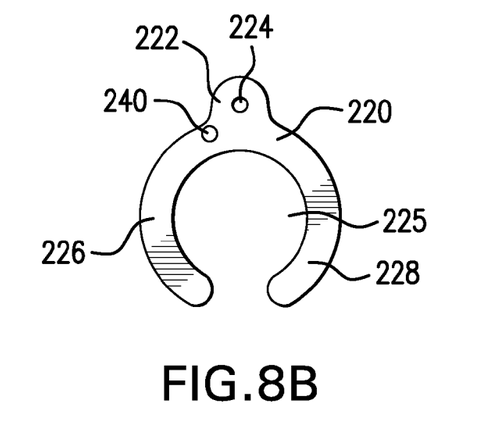

FIGS. 8A-8B show two embodiments of filter attachment 220. Filter attachment 220 is configured to be attached to compact loupe light 100 or any other suitable loupe light. In the embodiment shown in FIG. 8A, filter attachment 220 is substantially circular with a tab 222 which defines an attachment hole 224. Filter attachment 220 defines an opening 225 which is configured to fit completely around the end of a loupe light and is held in place by a press fit. Filter attachment 220 may alternatively be held in place by a set screw. In the embodiment shown in FIG. 8B, filter attachment 220 includes arms 226 and 228 which are configured to fit partially around the end of a loupe light and act like a clip to hold filter attachment 220 in place.

Filter 210 is coupled to filter attachment 220 by filter swivel 230. Filter swivel 230 fits through filter hole 214 and is fixed to attachment hole 224. Filter swivel 230 may be a pin, bolt, or any other suitable coupling that prevents filter 210 from separating from filter attachment 220. Alternatively, filter swivel 230 may be fixed to filter 210, or fixed to neither filter attachment 220 nor filter 210. Filter swivel 230 allows filter 210 to rotate freely.

Figure 9A:
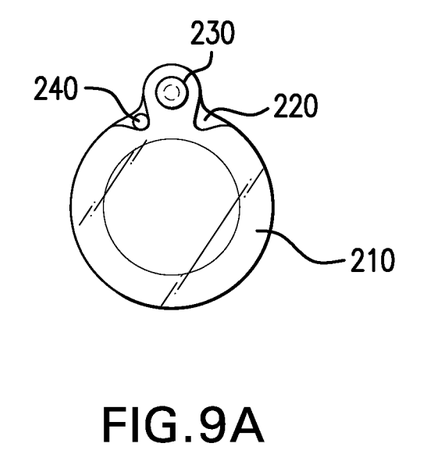
FIG. 9A shows a hands-free filter assembly with a filter in the in-use position.
Figure 9B:
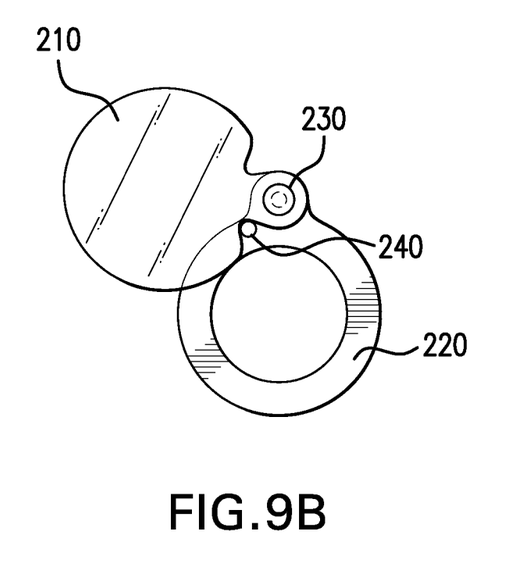
FIG. 9B shows a hands-free filter assembly with a filter in the non-use position.

FIG. 9A shows hands-free filter assembly 200 with filter 210 in the in-use position. FIG. 9B shows hands-free filter assembly 200 with filter 210 in the non-use position. Filter 210 moves between an in-use position, where it is filtering light from the loupe light, and a non-use position, where it is not filtering light from the loupe light. Filter 210 is moved when the user "flicks" his head to rotate filter 210. Filter 210 may thus be moved between the in-use and non-use positions without the need to manually manipulate filter 210.

Filter stop 240 prevents the rotation of filter 210 past a certain point. Filter stop 240 may be formed as part of filter 210, as part of filter attachment 220, or coupled to either as a separate component. In one embodiment, filter stop 240 maintains filter 210 in the in-use position. In another embodiment, filter stop 240 maintains filter 210 in the non-use position. In the embodiment shown, filter stop 240 is a pin coupled to filter attachment 220.

In the embodiment shown, filter 210 hangs down from filter swivel 230 when in the in-use position. Filter 210 is thus maintained in the in-use position by gravity. To move filter 210 to the non-use position, the user "flicks" his head to rotate filter 210 about filter swivel 230. Filter 210 rotates freely and comes to rest against filter stop 240. Filter 210 is thus maintained in the non-use position by gravity and filter stop 240. To move filter 210 back to the in-use position, the user "flicks" his head again to rotate filter 210 about filter swivel 230.

While the invention has been described in terms of some specific examples and in some specific embodiments, it will be clear that this invention is not limited to these specific examples and embodiments and that many changes and modified embodiments will be obvious to those skilled in the art without departing from the true spirit and scope of the invention as defined in the appended claims.

What is claimed is:

1. A filter assembly comprising:
 a filter;
 a filter attachment capable of being coupled to a loupe light;
 a filter swivel coupling the filter to the filter attachment, wherein the filter rotates freely about the filter swivel between an in-use position and a non-use position without manual manipulation, the filter having an axis of rotation substantially parallel to a longitudinal axis of the loupe light; and
 a filter stop coupled to the filter attachment, the filter stop capable of maintaining the filter in the non-use position.

2. The filter assembly of claim 1, wherein the filter attachment is configured to fit completely around an end of the loupe light.

3. The filter assembly of claim 2, wherein the filter attachment is held in place by a press fit.

4. The filter assembly of claim 2, wherein the filter attachment is held in place by a set screw.

5. The filter assembly of claim 1, wherein the filter attachment is configured to fit partially around an end of the loupe light.

6. The filter assembly of claim 1, wherein the filter swivel is a pin.

7. The filter assembly of claim 1, wherein the filter swivel is a bolt.

8. The filter assembly of claim 1, wherein the filter swivel is fixed to the filter attachment.

9. The filter assembly of claim 1, wherein the filter swivel is fixed to the filter.

10. The filter assembly of claim 1, wherein the filter swivel is fixed to neither the filter attachment nor the filter.

11. A method of using a filter assembly, the method comprising:
 providing a filter;
 providing a filter attachment capable of being attached to a loupe light;
 coupling the filter to the filter attachment with a filter swivel, wherein the filter rotates freely about the filter swivel between an in-use position and a non-use position without manual manipulation, the filter having an axis of rotation substantially parallel to a longitudinal axis of the loupe light;
 providing a filter stop coupled to the filter attachment, the filter stop supporting the filter in the non-use position;
 coupling the filter attachment to the loupe light worn by a user; and
 moving the filter between the in-use position and the non-use position without manual manipulation by flicking a head of the user.

12. A filter assembly for use with a loupe light, the filter assembly comprising:
 a filter attachment configured to be coupled to a light end of the loupe light without obstructing the light end of the loupe light;
 a filter having an in-use position in which the filter substantially covers the light end of the loupe light, and a non-use position in which the filter does not cover the light end of the loupe light, the filter defining a filter hole;
 a pin coupled to the filter attachment, the pin being substantially parallel to a longitudinal axis of the loupe light, the pin being positioned through the filter hole and allowing the filter to rotate freely about the pin between the in-use position and the non-use position, the pin being having a head configured to prevent the filter from separating from the filter attachment; and
 a filter stop coupled to the filter attachment, the filter stop configured to maintain the filter in the non-use position;
 wherein a user is able to move the filter between the in-use position and the non-use position without manual manipulation by flicking a head of the user.

13. The filter assembly of claim 12, wherein the light end of the loupe light is substantially circular, and wherein the filter attachment is substantially circular and fits around the light end of the loupe light.

14. The filter assembly of claim 12, wherein the filter attachment is substantially circular with a protruding attachment tab at or near a top of the filter attachment, the pin being coupled to the attachment tab, and wherein the filter is substantially circular with a protruding filter tab, the filter tab defining the filter hole.

15. The filter assembly of claim 14, wherein the filter hangs from the pin and is maintained in the in-use position by gravity.

16. The filter assembly of claim 12, wherein the filter rests on the filter stop and is maintained in the non-use position by gravity.

17. The filter assembly of claim 12, wherein the filter rotates more than 270 degrees between the in-use position and the non-use position.

* * * * *